(12) United States Patent
Schneider et al.

(10) Patent No.: US 6,404,500 B1
(45) Date of Patent: Jun. 11, 2002

(54) COLORIMETER APPARATUS AND RELATED PROCESS

(75) Inventors: David J. Schneider, Union, KY (US); Gary L Claypoole, Westchester; Johnny Michael Sandlin, South Lebanon, both of OH (US)

(73) Assignee: Aqua Check Systems, INC, Covington, KY (US)

( * ) Notice: Subject to any disclaimer, the term of this patent is extended or adjusted under 35 U.S.C. 154(b) by 0 days.

(21) Appl. No.: 09/236,827

(22) Filed: Jan. 25, 1999

(51) Int. Cl.[7] .............................................. G01N 21/59
(52) U.S. Cl. ...................................... 356/432; 356/436
(58) Field of Search ................................ 356/432, 433, 356/434, 345, 436, 437, 442

(56) References Cited

U.S. PATENT DOCUMENTS

| | | | |
|---|---|---|---|
| 4,970,671 A | 11/1990 | Rosenthal | 364/571.05 |
| 5,230,863 A | 7/1993 | Salpeter | 422/67 |
| 5,459,677 A | * 10/1995 | Kowalski et al. | 250/252.1 |
| 5,583,339 A | 12/1996 | Black | 250/339.13 |
| 5,606,164 A | 2/1997 | Price | 250/339.09 |
| 5,653,940 A | * 8/1997 | Carey et al. | 356/440 |
| 5,861,319 A | * 1/1999 | Lin et al. | 436/527 |

* cited by examiner

*Primary Examiner*—Richard A. Rosenberger
(74) *Attorney, Agent, or Firm*—Donald R. Bahr

(57) ABSTRACT

The disclosure of this invention relates to calorimeters and a process for operating a colorimeter. The colorimeter of the disclosure is controlled by a microprocessor which evaluates a predetermined radiation absorption curve for each sample. This is to be contrasted with the prior art wherein the test on a given sample evaluates only radiation absorption concentration points which are evaluated by the microprocessor. The colorimeter gives more accurate readings as a result of the fact that an absorption curve and its parameters are evaluated for each sample. The calorimeter uses multiple LEDs as a radiation source. The microprocessor further controls other functions of the colorimeter. A separate microprocessor may be used to control these other functions. The calorimeter and process of this invention are also useful in the analysis of samples for turbidity.

17 Claims, 3 Drawing Sheets

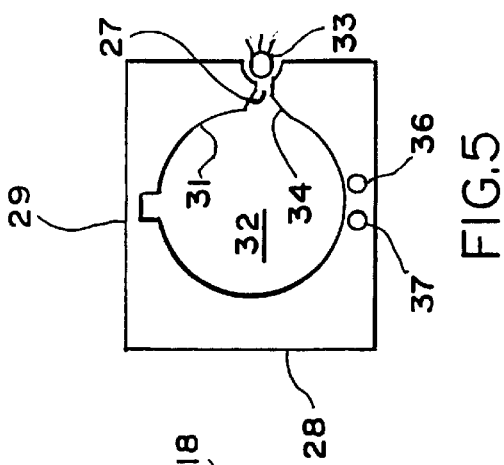
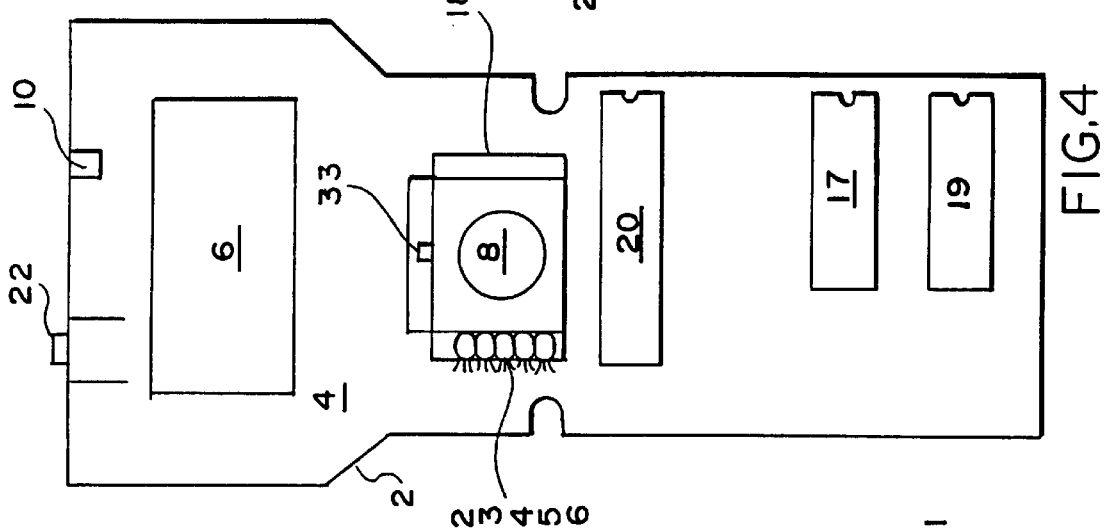
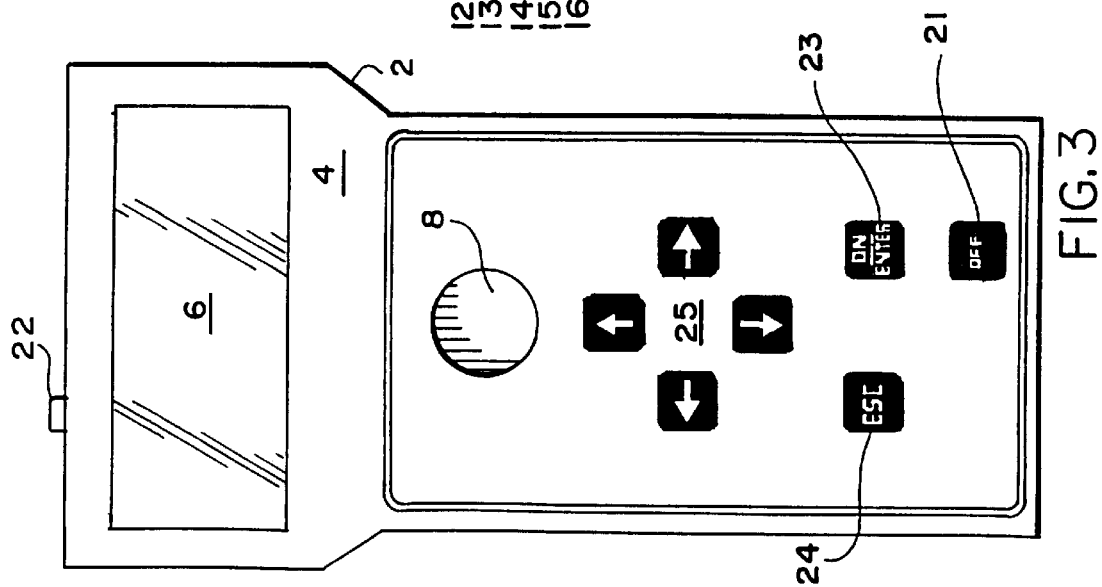

COLORIMETER APPARATUS AND RELATED PROCESS

FIELD OF THE INVENTION

This invention is concerned with colorimetry and more particularly, with apparatus and a process for conducting colorimetric analysis. In accordance with this invention, the analysis of a liquid or colloidal sample can be carried out with greater accuracy than has been possible in the prior art. The preferred aspects of this invention relate to the analysis of water samples in order to accurately determine the concentration of known substances such as the presence of chloride, fluoride ions etceteras. The apparatus and process of this invention uses photoelectric techniques.

BACKGROUND OF THE INVENTION

Colorimetric analysis of liquid samples has been a part of human technology since prehistory. In this regard, humans have used the color of a solution to determine the concentration of a known substance since man started preparing food. In this regard, humans through their ability to reason, have developed colorimetric analysis as a means of determining the properties of food in relation to a standard usually the personal preferences of an individual. An excellent example of this basic type of colorimetric analysis is the way individuals judge the strength of tea by its color. In this process a given individual develops a standard for his personal preference for tea by comparing his likes to a given color of a tea brew. Hence, the individual has developed a standard. The individual then compares this standard to the color of future tea brews in order to achieve his personal preferences. This mental process is the most basic form of colorimetric analysis. The process of this invention uses state of the art technology to carry out similar analyses to determine its concentration of a wide variety of analytes in solutions as may be contained in various liquids.

In the chemical arts, the term calorimeter refers to an instrument which compares the light transmitted through one solution to the light transmitted through a standard solution. Still another type of colorimeter is an instrument which is capable of measuring directly the amount of light energy which is absorbed by a solution. The first type of instrument is known as a color comparer while the second type is known as a photometer.

The most basic instruments consist of nothing more than a pair of matched tubes wherein one tube contains a standard solution. The more complicated instruments employ photoelectric cells and complex computing and electronic circuits in order to measure transmitted or absorbed light.

Solutions whose concentrations are to be determined by colorimetric techniques using the above described techniques need not be true solutions. The concentrations of colloidal solutions can also be determined by colorimetric technique if they are clear. However, when the solute particles are too large to form true solutions and hence, the solution appears turbid, measurements by true colorimetric techniques can be difficult.

This invention is concerned with an instrument and a related process which is capable of measuring concentrations by classic colorimetric techniques and for determining the relative turbidity of a solution. That is, the instrument and process of this invention is capable of measuring the relative haziness of a solution. More particularly, this invention is concerned with photoelectric apparatus and a related process which is capable of both colorimetric and turbidity analysis.

DESCRIPTION OF THE DRAWINGS

FIG. 3 is a plan view drawing showing the colorimeter of this invention.

FIG. 4 is a cutaway drawing along line 4—4 of FIG. 1 showing the colorimeter of this invention.

FIG. 5 is a plan section view illustrating the turbidity aperture of the sample receiving chamber.

BRIEF DESCRIPTION OF THE INVENTION

Figure 1:
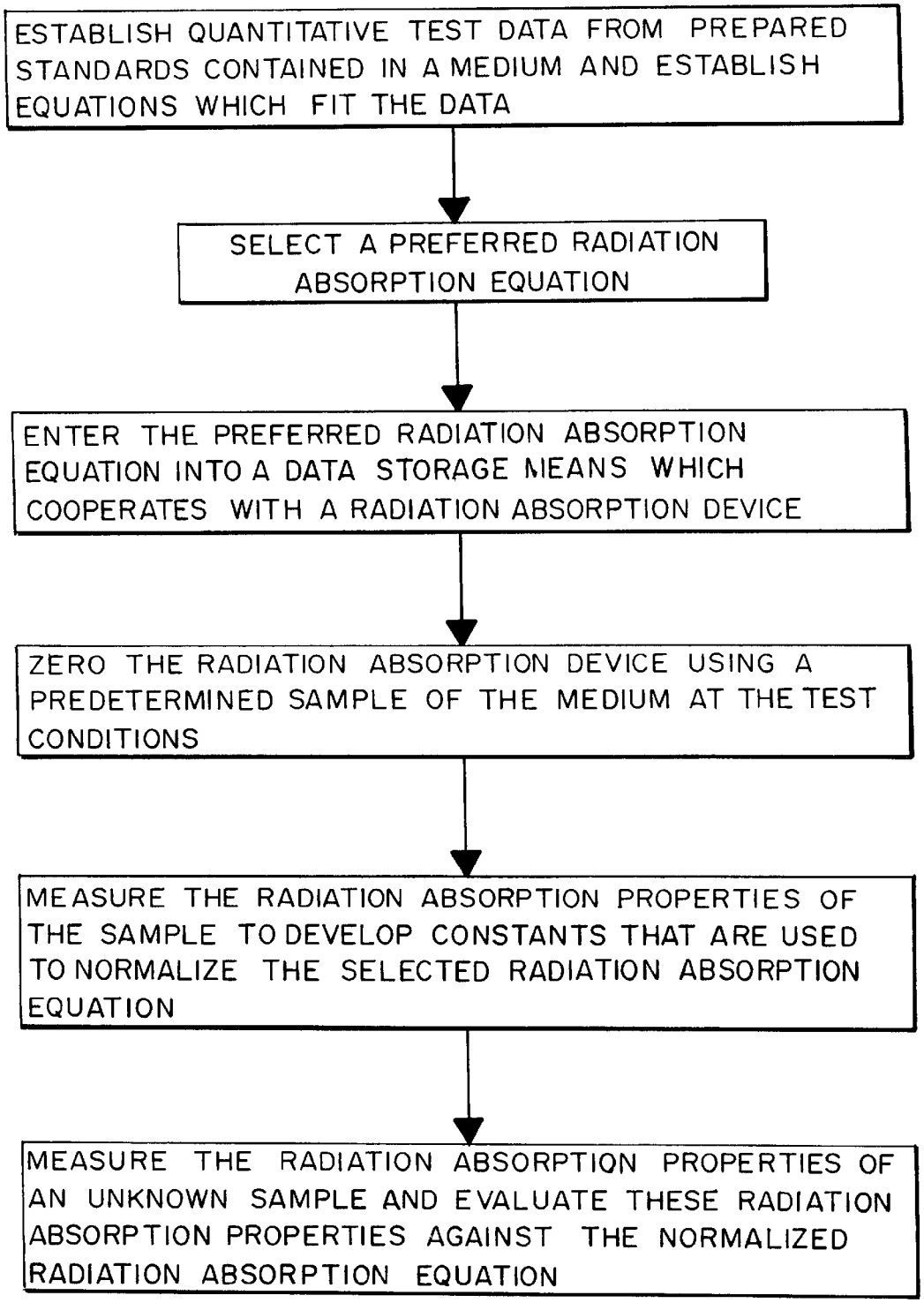
FIG. 1 is a box diagram showing the process of this invention.

The ability to test solutions for known analytes is of the utmost importance to modern society. In particular, the ability to test public water supplies for various desirable and undesirable analytes is a necessary prerequisite for public health.

For example, the introduction of fluorine, as the fluoride ion, into public water supplies has been found to be beneficial for dental health. The beneficial properties of the fluoride ion in public water supplies are evident only if the fluoride ion is present in the proper concentration. In fact, if the fluoride ion is present in excess concentrations it is detrimental to dental health. Accordingly, in public water supplies it is necessary to have a test instrument and process whereby the concentration of various analytes can be determined quickly and easily by relatively untrained personnel. This invention achieves these ends.

The invention relates to a photoelectric calorimeter and a related process whereby the concentration of various analytes can be determined in a quick and easy fashion.

The photoelectric calorimeter of this invention is integrated with a computer in such a manner that a radiation absorption curve is evaluated in regard to each individual sample in order to make a quantitative evaluation of the presence of a particular analyte. This is to be compared with the prior art wherein a radiation absorption curve is not evaluated in each instance but instead only points of the radiation curve are entered into the database.

The process and photocolorimeter of this invention wherein the radiation absorption curve is evaluated in each test is superior to the prior art, as with the process of this invention variations in the base samples can be factored into the quantitative evaluation. That is, the apparatus or process of this invention allows the variables of the total sample to be evaluated in each quantitative analysis.

For example, a given water sample from a public water supply may contain thirty or forty different analytes which will vary from one public water supply to another public water supply. These variations result usually from the different geology in the vicinity of the water supply and from different analytes which have been added to the water supply. When a technician is trying to analyze a sample for a particular ion for example, the fluoride ion, the presence of other analytes may interfere with an accurate colorimeter analysis of the sample for the fluoride ion. In the prior art the variations in the samples are not considered, as prior art calorimeters only refer to the individual concentration points entered into the database. In the calorimeter and process of this invention, individual points of an absorption curve are not consulted with each analysis but instead the absorption curve in toto is evaluated in each instance.

As a result of this evaluation of the absorption curve in each instance more accurate analysis are obtained as the variables of each base sample is evaluated in making the analysis for each individual analyte.

DETAILED DESCRIPTION OF THE PREFERRED EMBODIMENT

In accordance with the above discussion this invention is concerned with a calorimeter and a related process for quantitatively analyzing a solution for a known analyte. As used in this application, the term analyte will be used to describe metallic, non-metallic, organic, and inorganic ions and properties such as pH and turbidity.

As to this invention, the term analyte will include, but is not limited to:

1. Properties such as acidity, alkalinity, pH 6.4 to 9.6, turbidity low, turbidity medium and turbidity high;
2. Dissolved organic molecules such as hydrazine, phenol, cyanide, lignin, tannin, linear alkyl, benzene sulfonate, and chloramine-T;
3. Dissolved cations such as aluminum, ammonia, barium, boron, calcium, calcium copper, chromium total, hex chromium, iron, lead, magnesium, manganese low, manganese high, mercury, molybdenum, nickel, potassium, selenium, silver sodium and zinc;
4. Dissolved anions such as chloride, fluoride low, chlorine, bromine, fluoride high, iodine, nitrate low, nitrate high, nitrite, orthophosphate low, orthophosphate high, silica low, silica high, sulfate low, sulfate high, sulfide, hypochlorite;
5. And dissolved gasses such as chlorine, oxygen, carbon dioxide, bromine and ozone.
6. Gaseous mixtures or gases dissolved in other gasses such as in air or the analysis of the exhaust gasses from an internal combustion engine.

As is briefly discussed above, colorimetry is the observation or measurement of transmitted or absorbed radiant energy. The observation or measurement of the radiant energy can be by the human eye or by a photoelectric cell. This invention is concerned with colorimeters which use photoelectric cells. The use of photoelectric cells to measure the intensity of the radiant energy is advantageous as errors due to the personal characteristics of each human observer are eliminated.

In running analytical tests on analytes such as those mentioned in points 1 to 6 above, prior art devices and process only blanked the test protocol for local conditions usually local water conditions. In contrast, the process and apparatus of this invention normalizes the test protocol for all variables present at the time of the test.

The use of photoelectric cells in colorimeter analysis is approximately fifty years old. As a source of radiant energy the calorimeter of this invention uses multiple light emitting LEDs.

LEDs which are useful in the process and apparatus of this invention are:

| | | |
|---|---|---|
| 1. Ga AlP | 620 ± 35 mm |
| 2. Ga As P | 590 ± 35 mm |
| 3. Ga P | 565 ± 40 mm |
| 4. Ga Al As | 880 ± 50 mm |
| 5. Ga As | 940 ± 50 mm |
| 6. Ga N | 430 ± 65 mm |

Wherein N=Nitrogen, Ga=Gallium, Al=Aluminum, As=Arsenide, In=Indium and P=Phosphorus.

The process of this invention relates to the manner in which the absorption or transmission data for the radiant energy is processed.

As is discussed above, the use of photoelectric cells in colorimeters is old in the art. In the prior art a filament is used to produce a band of visible light. This band of visible light was then altered in each test by the placement of a filter in the beam of radiant energy in order to alter the beam of radiant energy so as to make it suitable for the particular test being conducted. In contrast to the mechanical placement of filters in the beam of radiant energy, the apparatus of this invention uses multiple LEDs which either singularly or in combination produce a beam of radiant energy which is suitable for the test being conducted. In other words, the apparatus of this invention uses one or more LEDs as described above to produce a beam of radiation having the proper wavelength and intensity for the test to be conducted. With this arrangement the need to mechanically place and remove filters in the radiation beam is eliminated.

As a further means of producing a beam of radiation which is suited for a particular test, the amperage and the voltage and combinations thereof, can be varied to one or more LEDs.

While single LEDs have been used in prior art colorimeters, the use of multiple LEDs in calorimeters is not known. The use of a diode as a source of radiant energy is advantageous in that LEDs stabilize immediately and the radiation emissions of an LED shows minimal temperature sensitivity. In contrast, filament based sources of radiant energy take many minutes to stabilize and the output is very temperature dependent. The consistency of LEDs as a source of radiant energy is very important for example, in a public water department or with outdoor measurements where the temperature at which tests are being conducted can vary over fifty (50) plus degrees centigrade.

Further, LEDs are advantageous in that they use approximately one tenth the energy needed to power a filament source of radiant energy. This part is particularly important when the resulting instrument is meant to be portable and hence is battery powered.

Colorimeter tests are conducted on colored solutions. While some solutions are naturally colored, for example, the blue color of some copper containing solutions, in most instances the analytes being tested do not produce colored solutions. For example, a water solution of sodium chloride, table salt, is clear, therefore, in order to test for the sodium and chloride ions it is necessary to alter the solutions in such a manner that the sodium or chloride ions produce a visible color change in the solution. This end is accomplished by adding to the clear solution a reagent which will react only with the chloride ions to produce a colored solution.

Particular reagents which are specific for particular analytes, which when added to a solution produce a colored solution are well known in the prior art. For the analytes which are listed above specific reagents and sample preparation protocols are identified in references such as;

1. *Standard Methods for the Examination of Water and Wastewater*, 18$^{th}$ Edition 1992, Prepared and published jointly by American Public Health Association, American Water Works Association, Water Environment Federation
2. *Colorimeter Determination of Traces of Metal*, Third Edition Revised and Enlarged, E. B. Sandell, Ph.D.
3. *Colorimeter Chemical Analystical Methods*, 8$^{th}$ Edition 1974, L. C. Thomas, B.Sc., F.R.I.C., G. J. Chamberlin.
4. U.S. EPA. 1993, *Methods for the Determination of Inorganic Substances in Environmental Samples*. U.S. Environmental Protection Agency, Office of Research and Development, Environmental Monitoring Systems Laboratory, Cincinnati, Ohio, EPA/600/R-93/100.) NTIS: PB94-120821).
5. ASTM *Standard Colorimeter Test Protocols.*

Referring to FIGS. 3 to 5, it can be seen that calorimeter 2 comprises a case 4, a screen 6, a sample receiving chamber 8, a power source 10, LEDs 12, 13, 14, 15 and 16, and a radiation absorption cell 18. The exterior of colorimeter 2 further includes a power switch 21 and a plurality of control switches 23, 24 and 25.

In operation, colorimeter 2 is calibrated with a standard base sample which in the case of a public water supply is a water sample to which coloring reagents have not been added.

A sample to be tested is then treated with a reagent in accordance with published protocols as are referred to above. Note the test reagent or reagents are specific for the analyte, which is being tested for. A vial of the prepared sample is then placed in receiving chamber 8. One or more of LEDs 12, 13, 14, 15 or 16, is then activated by applying electrical power thereto. The number, nature of and the amount of electric power has been predetermined and programmed into the EPROM of FIG. 2 in order to produce the optimum wave length and intensity of radiant energy for the test being conducted. The radiation being absorbed by the sample is then determined by comparing the output of one or more LEDs 12, 13, 14, 15 and 16 with the energy being absorbed by radiation absorption cell 18. This difference is then visually recorded as a concentration on screen 6. This conversion is effected by converting the output of absorption cell 18 into voltage, amperage, digital waveform, etc.

The evaluation of the output of LEDs 12, 13, 14, 15, and 16 and the absorption by radiation absorption cell 18 is done with a preselected radiation absorption curve by a microprocessor 20 which may be integral with colorimeter 2. The memory of the microprocessor 20 is loaded with multiple programs which control the operation of colorimeter 2. These programs will include at least a program to operate colorimeter 2 in accordance with a predetermined test protocol, in order to test for a specific analyte.

In addition, the microprocessor is loaded with a program to select the most appropriate radiation curve for testing a given analyte and then comparing the radiation absorption properties of the analyte against the selected radiation absorption curve.

Likewise, the microprocessor is loaded with a program to control the wavelength output of the LEDs and to select which and how many LEDs will be used.

Further, the microprocessor 20 may include a program which will allow it to communicate with an extended computer through an integral data port 22, for example, to download all data accumulated in RAM processor 19 over a given period of time. The preferred data port for use in calorimeter 2 is an RS-232 port. EPROM 17 is also provided.

The process of this invention relates to how the data generated by a radiation absorption cell 18 is correlated into a quantitative evaluation of the concentration of the analyte in the sample.

Figure 2:
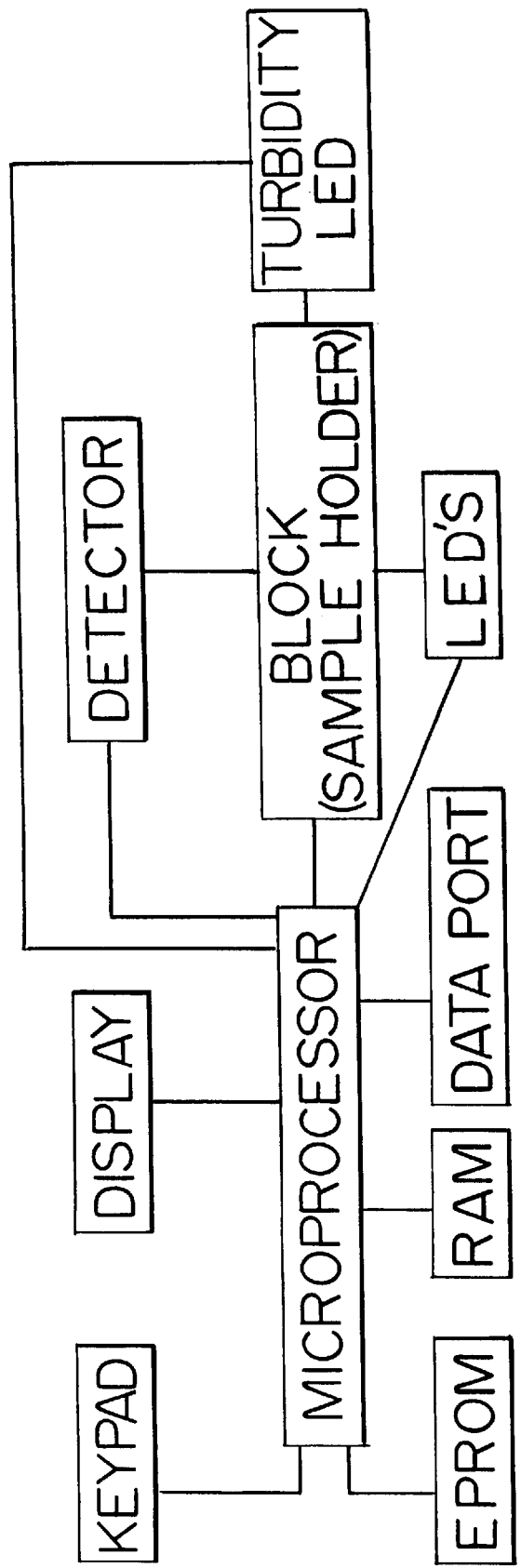
FIG. 2 is a box diagram showing the general layout of the electronic components as are used in the apparatus of this invention.

FIG. 2 is a block diagram showing the general layout of the electronic components of colorimeter 2.

In the prior art, the data generated by radiation absorption cell 18 is compared to a set of parameters for each analyte which is programmed into a database which is integral with the prior art colorimeter. This prior art database comprises a predetermined set of x values concentration in ppm and y values, y counts of radiation which are transmitted through the sample. The x and y values are determined from separately prepared samples at various concentrations and are loaded into the data base before the test on the unknown sample is made. It should be noted that a separate set of x and y values must be obtained for each analyte to be tested. That is, in the prior art empirical data is generated and stored in the data base.

In contrast to entering the x and y values into the database, in the process of this invention a predetermined absorption equation is normalized for each sample tested. This normalization allows the process of this invention to account for the variables which are inherent in any colorimeter testing procedure.

The variables which are accounted for in the normalization of the absorption equation for each sample are:

1. Variables in the quality and dimensions of the sample container.
2. Contamination on the surface of the sample container for example, fingerprints.
3. The age of the radiation source which will vary with the number of hours it has been used.
4. The position of the radiation source in relation to the sample container. For example, if colorimeter 2 is dropped, LEDs 12, 13, 14, 15 and 16 or radiation absorption cell 18 may be jarred out of position in relation to each other. Any movement of these elements from a predetermined calibration point will affect the accuracy of the analysis of the analyte.
5. Fluctuations in the power supplied to LEDs 12, 13, 14, 15 and 16. For example, in a portable battery powered instrument the age or temperature of the battery.
6. Variations in the test medium. For example, variations in a water source for a public water supply from location to location.
7. Variations in manufacture of the alignment of the LEDs to radiation absorption cell 18. Further, as a result of the fact that the alignment of the LEDs to the radiation absorption cell is not crucial, the alignment of the components need not be absolutely uniform and, hence, manufacturing cost are lowered.
8. Colorimeter 2 need not be pre calibrated during the manufacturing process and hence, manufacturing costs again are lowered.
9. There is no need to recalibrate calorimeter 2 if it is abused for example, by dropping.

In using the process of this invention, greater accuracy is achieved in the analysis of the analyte. Using the prior art method wherein predetermined data points are loaded into a database interpolation of these data points in relation to the sample is needed. In the process of this invention all points continuous to the curve at any point are evaluated to arrive at an exact point and hence, an exact concentration. As a result, the accuracy of tests conducted in accordance with the process of this invention averages 0.998 (1=perfect fit) by the Chi-Squared statistical method.

In the process of this invention, possible errors which may result from variables 1 to 9 as described above, are eliminated by calculating new constants for introduction into the radiation absorption equation which is selected for each test. The new constants are generated when the radiation device is zeroed with the test medium or with a predetermined standard. When these new constants are calculated and entered into the radiation absorption equation, errors which result from variables 1 to 9 as described above, are eliminated or greatly reduced.

Further, in order to eliminate "one event" errors the process of the invention incorporates a multi-test system into the test protocol such that anomalous test data is eliminated.

In this procedure, colorimeter 2 runs a series of tests until the results from a given number of tests are within a predetermined value from the previous value. When this predetermined value is achieved, colorimeter 2 runs a final test from which the concentrations of the analyte is determined.

When the process of this invention is used, the whole test procedure may be controlled by a microprocessor. In contrast to the prior art there is no need to mechanically position a filter in the radiation beam in order to achieve the optimum radiation band for the test to be conducted. Instead, each test procedure has an optimum radiation band programmed into the test protocol. This optimum radiation band is then achieved by the microprocessor selecting the proper LED or combination of LEDs and then selecting and controlling the proper voltage or amperage to the LEDs in order to achieve the optimum radiation wave length or intensity. Power to the LEDs is controlled by a constant current source. By use of a constant current source, improved accuracy is achieved by eliminating changes in the LED output over time.

In the prior art, once radiation is absorbed it is converted to voltage which is read on a voltmeter the scale of which is calibrated in concentration. This procedure can likewise be used with this invention.

In the preferred process of this invention, the output of radiation absorption cell 18 may be converted directly into digital wave form whereupon the frequency of this digital wave form is measured in order to measure the concentration of the analyte in the test medium.

The advantage of converting the output of radiation absorption cell into digital waveform is that frequency output is linear over a wide range of light intensities. This linear relatively allows for better accuracy in determining the concentration of the analyte. Further, the need to convert the data from an analog to a digital format is eliminated.

The preferred radiation absorption equations, for use with the process of this invention are linear equations, logistic model equations and exponential equations.

Still other types of equations which are applicable to the process of this invention are Bleasdale model equations, rational functions equations, sinusoidal functions equations, polynomial equations, quadratic equations, reciprocal of quadratic equations, Harris model equations, Richards model equations, modified power model, and reciprocal model, equations.

The preferred linear equation for use in the process of this invention is;

$$Y=bx+a$$

Wherein y is the relative amount of light passing through sample.

Wherein a is a constant which reflects the variables in the test medium and other physical parameters determined at the zeroing stage. Wherein x is the amount of analyte in sample in PPM or percent, percent transmittance or percent absorption.

Wherein b is a constant which is developed when the preferred radiation absorption equation is selected.

The preferred logistic equation for use in the process of this invention is;

$$y = \frac{a}{1+be^{cx}}$$

Wherein y is the relative amount of light passing through the sample.

Wherein b is a constant which is developed when the preferred radiation absorption equation is selected.

Wherein x is the amount of analyte in sample in PPM or percent, percent transmittance or percent absorption.

Wherein a is a constant which reflects the variables in the test medium and other physical parameters determined at the zeroing stage.

The preferred exponential equation for use in this invention is $$y=ae^{bx}$$

Wherein y is the relative amount of light passing through the sample.

Wherein a is a constant which reflects the variables in the test medium and other physical parameters, determined at the zeroing stage.

Wherein b is a constant which is developed when the preferred radiation absorption equation is selected.

Wherein x is the amount of analyte in sample in PPM or percent, percent transmittance or percent absorption.

Referring to FIG. 1, it can be seen that the process of this invention for qualitatively analyzing a gaseous or liquid medium by radiation absorption for a known analyte comprises the steps of;

1. For said analyte establishing quantitative test data in the medium for said analyte using prepared standards over a range of concentrations.
2. Entering the test data into an electronic processor to establish multiple radiation absorption equations that conform to the test data.
3. Selecting a preferred radiation absorption equation.
4. Entering said preferred radiation absorption equation into a data storage means which cooperates with a radiation absorption device.
5. Zero the radiation absorption device using a predetermined concentration standard of said medium.
6. Measure the radiation absorption properties of said standards to develop constants that are used to normalize the radiation absorption equation.
7. Position an unknown sample containing an analyte in said medium in said radiation absorption device and evaluate the absorption properties of the sample against the normalized radiation absorption equation. This evaluation may be carried out by a microprocessor.

The results of the evaluation of steps one to seven above may be converted into an electrical current, voltage or radio frequency radiation, to determine the concentration of the analyte in the medium.

Further, if a microprocessor is used to evaluate the radiation absorption of the sample as per step seven above, the microprocessor through a communication port may interact directly with a generator of radio frequency band radiation for conversion of the data directly into digital waveform. The concentration of the analyte is then determined by reference to a linear graph of the digital waveform where x is the concentration of the analyte and y is the frequency of the digital waveform.

Further, the unknown sample of step 7 above may be treated with a reagent prior to positioning the sample in the radiation absorption device, in order to alter the radiation absorption properties of said sample. In most instances the reagent causes the sample to become colored and, hence, the radiation absorption properties are altered. The treating of a sample in this manner is in accordance with the above described sample preparation procedures.

Referring to FIG. 5, this invention further includes a special turbidity sample holder 28 which may be used in colorimeter 2 or in a dedicated turbidity meter. Turbidity tests are generally conducted on water samples to determine if it is hazy or cloudy. Turbidity in water samples results when particles become collodial in nature. It is unexpected that colorimeter 2 of this invention is also useful in conducting turbidity tests.

Sample holder 28 includes a detector 29 which is capable of detecting radiation in the range of 525±30 nm for purposes of evaluating the turbidity of a given sample. LED 33 is positioned in an aperture 27 which communicates with the interperiphery 31 of a sample receiving chamber 32. LED 33 is recessed back from the interperiphery 31 of receiving chamber 32 in aperture 27. Area 34 of aperture 27 proximate periphery 31 is conical. The preferred cone having an angle of 15 degrees. The conical portion 34 aids in the dispersion of radiation emitted by LED 33 into sample receiving chamber 32 thereby permitting a greater portion of the radiation emitted by LED 33 to impinge on detector 29. LED 33 and detector 29 may be positioned in relation to each other at an angle of from about 60 to about 120 degrees with the preferred positioning being 90 degrees.

Sample holder 28 may further include one or more LEDs 36 and 37 which also impinge on detector 29 for purposes of conducting colorimetric analysis in accordance with the description hereinabove.

EXAMPLES

The present invention is illustrated by the following Examples which, however, are not to be constructed as limiting the invention to their details.

Example 1

Fluoride Low

Fluoride was chosen as the analyte for this example. The fluoride test protocol was adapted from the *Standard Methods* (18$^{th}$ addition, 1992) version for fluoride analysis using the SPADNS method. The diode utilized was yellow-orange and emitted radiation at a wavelength of approximately 610 nm+/−35 nm. Quantitative test data was obtained using nine prepared standards containing fluoride in the range 0.00–2.00 ppm. A range of 0.00–2.00 is the standard range for testing fluoride through colorimetric analysis due to a target range for most water supply municipalities being 0.80–1.20 ppm fluoride in the water supply. Standard solutions at concentrations of, 0.00, 0.20, 0.50, 0.80, 1.00, 1.20, 1.50, 1.80 and 2.00 ppm were used. Using calorimeter 2 in a continuous diode output mode, data points representing relative counts in the amount of light passing through each sample were recorded for each standard solution. Using x to represent the standard solution in ppm and y to represent the relative amount of light passing through the sample, the following pairs of data were collected;

TABLE I

| x (ppm) | y (relative counts) |
|---|---|
| 0.00 | 2788 |
| 0.20 | 2962 |
| 0.50 | 3255 |
| 0.80 | 3598 |
| 1.00 | 3761 |
| 1.20 | 3932 |
| 1.50 | 4130 |
| 1.80 | 4223 |
| 2.00 | 4289 |

In order to correlate the data of Table I, a mathematical curve fitting program (CurveExpert version 1.34, 1997) was utilized. The data set in Table I was entered into the curve fitting program in order to determine a best fit for the data. The curve fitting program uses standard mathematical principles to arrive at the best equation which represents the given data. The preferred equation was determined by looking at the best fit to the data using standard statistical methods of analysis, such as linear and non-linear regression models. In this example and for the data listed in Table I, the preferred radiation absorption equation was the Logistic Model with a chi-squared correlation of 0.99839 (1.00 being an exact fit to the data). The Logistic Model is represented by the equation: $y=a/(1+be^{-cx})$. Coefficients generated under this curve fitting routine were a=4687.33, b=0.70488 and c=1.0491. Fluoride was chosen to be zeroed at 1.00 ppm because most municipal water plants try to keep fluoride levels between 0.80 and 1.20 ppm fluoride and therefore standards of 1.00 ppm are generally used for zeroing. It should be noted that the calorimeter of the current art can be programmed to zero at any point in the range and still retain accuracy. The a constant generated during each zeroing is normalized by dividing it by the y value at 1.00 ppm (3761). Therefore, the a value generated at each test zeroing will be divided by 1.2463, the value obtained when dividing a=4687.33 by the 1.00 ppm y value 3761.

An important note is the other constants, b and c, from the Logistic Model equation above remain constant over the range tested.

Along with the preferred radiation absorption equation, the constants b and c as well as the normalization factor for fluoride 1.2463 are entered into the calorimeter 2 and stored into memory.

During each test zeroing a new a value is generated. This a value is normalized by the factor 1.2463 in order to generate a value for the zeroing standard at 1.00 ppm.

For example, if the a factor is 4,500 then a will be normalized with 1.2463 and the value for the zero (in this case at 1.00 ppm) will be 3610.68. In this process the radiation absorption equation is normalized to all conditions before each test sample has been evaluated. The a values can be lower or higher depending on environmental conditions, life of the LEDs, alignment of the colorimeter, and other physical factors. However, the normalized value after zeroing the colorimeter, will produce results for unknown samples as good as the curve fit correlation, in this case 0.99839.

After the constants b, c and the normalization factor 1.2463 is entered into the memory of the colorimeter, tests on samples can be run. The following tests were conducted to test the accuracy of the colorimeter:

A test was run to see how temperature variation effects results. Tests were conducted at 69° F. and 15° F. The colorimeter of this invention was called Colorimeter A and a commercial prior art colorimeter manufactured by LaMotte Company (model: smart, serial #1613-0298) was Colorimeter B. Both colorimeters and reagent standards were placed outside for 30 minutes before running the lower temperature experiment. A 1.00 ppm standard fluoride experiment was conducted with results averaged over 5 tests as follows:

| Colorimeter A Average Results | | | Colorimeter B Average Results | | |
|---|---|---|---|---|---|
| 69° F. | 15° F. | % Difference | 69° F. | 15° F. | % Difference |
| 0.99 ppm | 1.00 ppm | 1.0% | 0.95 ppm | 0.83 ppm | 12.6% |

The colorimeters and reagents were brought back to 69° F. and tests were conducted again with the same results as recorded above for the 69° F. temperature.

The colorimeters were now kept at 69° F. and the reagents were left to stand at 18° F. for 1 hour. The following shows the results from this experiment:

| Colorimeter A Average Results | | | Colorimeter B Average Results | | |
|---|---|---|---|---|---|
| 69° F. | 18° F. | % Difference | 69° F. | 18° F. | % Difference |
| 0.99 ppm | 1.00 ppm | 1.0% | 0.95 ppm | 0.86 ppm | 9.4% |

It can be seen from this example that the temperature of the art calorimeter of this invention and/or the reagent temperature at the time of measurement is not effected by ambient temperature. Further, by use of this invention, more consistent results are achieved when compared to the prior art.

Example 2

Zinc

Zinc was chosen as the analyte for this example. The zinc test method was adapted from the Standard Methods (18$^{th}$ addition, 1992) version for zinc analysis (Zincon method). The diode utilized was red and emitted radiation at a peak wavelength of approximately 660 nm, +/−20 nm. Quantitative test data was obtained using eight prepared standards containing sulfate low in the range 0.00–2.00 ppm. These standard solution concentrations were, 0.00, 0.20, 0.50, 0.80, 1.00, 1.20, 1.50, 2.00 ppm. Using colorimeter 2 in a continuous diode output mode, data points representing relative counts in the amount of light passing through each sample were recorded for each standard solution. Using x to represent the standard solution in ppm and y to represent the relative amount of light passing through the sample, the following pairs of data were collected;

TABLE II

| x (pH) | y (relative counts) |
|---|---|
| 0.00 | 5025 |
| 0.20 | 4355 |
| 0.50 | 3755 |
| 0.80 | 3218 |
| 1.00 | 2924 |
| 1.20 | 2634 |
| 1.50 | 2308 |
| 2.00 | 1936 |

In order to correlate the data of Table II, a mathematical curve fitting program (CurveExpert version 1.34, 1997) was utilized. The data set in Table II was entered into the curve fitting program in order to determine a best fit to the data. The curve fitting program uses standard mathematical principles to arrive at the best equation which represents the given data. The preferred equation was determined by looking at the best fit to the data using standard statistical methods of analysis, such as linear and non-linear regression models. In this example and for the data listed in Table II, the preferred radiation absorption equation was the Logistic model ($y=a/(1+be^{-cx})$) with a chi-squared correlation of 0.99952 (1.00 being an exact fit to the data). Coefficients generated under this model were $a=-2265.29$, $b=-1.45305$ and $c=-0.20268$. Since zinc was chosen to be zeroed at 0.0 ppm, the a constant generated during each zeroing is normalized by dividing it by the y value at 0.0 ppm (5025). Therefore, the a value generated at each test zeroing will be divided by −0.4508, the value obtained when dividing $a=-2265.29$ by the 0.0 ppm zero 5025.

An important note is the b and c constants remains constant over the range tested. Along with the preferred radiation absorption equation, the constants b and c, as well as the normalization factor for zinc −0.4508 are entered into the colorimeter 2 and stored into memory. During each test zeroing a new a value is generated. This a value is normalized with the factor −0.4508 in order to generate a value for the zeroing standard at 0.0 ppm. For example, if the a factor is 3,000 then a will be normalized with 0.4508 and the value for the zero (in this case at 0.0 ppm) will be 6654.84 (note: the absolute value of the number is used for y counts). In this process the radiation absorption equation is normalized to all conditions before each test sample has been evaluated. The a values can be lower or higher depending on environmental conditions, life of the LEDs, alignment of the calorimeter, and other physical factors. However, the normalized value after zeroing the calorimeter, will produce results for unknown samples as good as the curve fit correlation, in this case 0.99952.

A test was run to see how newly manufactured calorimeters of this invention measured the same analyte with no calibration of any kind. Tests were conducted on three calorimeters using the same analyte, zinc. The colorimeters were labeled Colorimeter 1, Colorimeter 2 and Colorimeter 3. A 1.00 ppm standard zinc experiment was conducted with results averaged over 5 tests as follows:

| Colorimeter 1 Averaged Results: | Colorimeter 2 Averaged Results: | Colorimeter 3 Averaged Results: |
|---|---|---|
| 0.994 ppm | 0.986 ppm | 1.002 ppm |

Variance of averaged results to 5 tests: 0.00004266

It can be seen from this experiment that calibration is not needed with calorimeters of this invention and that accuracy from one manufactured colorimeter to another is excellent.

Example 3

Ammonia

Ammonia was chosen as the analyte for this example. The ammonia test method was adapted from the Standard Methods (18$^{th}$ addition, 1992) version for ammonia analysis (Nessler method). The diode utilized was blue and emitted radiation at a peak wavelength of approximately 430 nm, +/−65 nm. Quantitative test data was obtained using eleven prepared standards containing ammonia in the range 0.00–5.00 ppm. Most ammonia field analysis is in this range (example: aquaculture fish farms). These standard solution concentrations were, 0.00, 0.50, 0.80, 1.00, 1.20, 1.50, 2.00, 2.50, 3.00, 4.00, 5.00 ppm. Using calorimeter 2 in a continuous diode output mode, data points representing relative counts in the amount of light passing through each sample were recorded for each standard solution. Using x to represent the standard solution in ppm and y to represent the relative amount of light passing through the sample, the following pairs of data were collected;

TABLE III

| x (ppm) | y (relative counts) |
|---------|---------------------|
| 0.00    | 2476                |
| 0.50    | 2274                |
| 0.80    | 2185                |
| 1.00    | 2099                |
| 1.20    | 2015.5              |
| 1.50    | 1903                |
| 2.00    | 1734.5              |
| 2.50    | 1613.5              |
| 3.00    | 1475.5              |
| 4.00    | 1261                |
| 5.00    | 1060                |

In order to correlate the data if Table III, we used a mathematical curve fitting program (CurveExpert version 1.34, 1997). The data set in Table III was entered into the curve fitting program in order to determine the best fit to the data. The curve fitting program uses standard mathematical principles to arrive at the best equation which represents the given data. The preferred equation is determined by looking at the best fit to the data using standard statistical methods of analysis, such as linear and non-linear regression models. In this example and for the data listed in Table II, the preferred radiation absorption equation was the exponential model ($y=ae^{bx}$) with a chi-squared correlation of 0.999547 (1.00 being an exact fit to the data). Coefficients generated under this model were a=2479.08, b=−0.17148. Since ammonia was chosen to be zeroed at 0.00 ppm, the a constant generated during each zeroing is normalized by dividing it by the y value at 0.00 ppm (2476). Therefore, the a value generated at each test zeroing will be divided by 1.0012, the value obtained when dividing a=2479.08 by the 0.00 ppm zero 2476.

An important note is the b constant remains constant over the range tested. Along with the preferred radiation absorption equation, the constant b, as well as the normalization factor for ammonia 1.0012 are entered into the colorimeter 2 and stored into memory.

During each test zeroing a new a value is generated. This a value is normalized with the factor 1.0012 in order to generate a value for the zeroing standard at 0.00 ppm.

For example, if the a factor is 2,800 then a will be normalized with 1.0012 and the value for the zero (in this case at 0.00 ppm) will be 2796.64. In this process the radiation absorption equation is normalized to all conditions before each test sample has been evaluated. The a values can be lower or higher depending on environmental conditions, life of the LEDs, alignment of the colorimeter, and other physical factors. However, the normalized value after zeroing the calorimeter, will produce results for unknown samples as good as the curve fit correlation, in this case 0.999547.

Using the same analyte, ammonia, but using the linear equation (y=a+bx) which has less correlation to the data set than the exponential equation we have the following:

The chi-squared correlation using the linear model is 0.99049. Coefficients generated under this model were a=2381.18, b=−283.533. The normalization factor is this case is 0.96170. Therefore, the a value generated at each test zeroing will be normalized by 0.96170.

This example demonstrates that more than one equation can be used for the data and a given analyte. Therefore, these equations can be stored into the memory and used by the colorimeter of this invention.

Example 4

Copper

Copper was chosen as the analyte for this example. The copper test method was adapted from the Standard Methods ($18^{th}$ addition, 1992) version for copper analysis (Bathocuproine method). The diode utilized was blue and emitted radiation at a peak wavelength of approximately 430 nm, +/−65 nm. The preferred radiation absorption equation was the Logistic model. The colorimeter was calibrated in a similar way as mentioned in the previous examples, however this time using copper standards.

This example shows another useful aspect of this invention as compared to the prior art. All prior art calorimeters are susceptible to stray light reaching the receiving chamber, and therefore the detector, unless the chamber and sample are covered. This stay light can produce erroneous results by interfering with the detector and recording differing amounts of light detected depending on ambient light conditions. Using the current art calorimeter, this stray light susceptibility is minimized by the normalization process. Each test zeroing normalizes the preferred equation stored in the colorimeter. Therefore, the stray light that may be present upon zeroing is factored into the normalization and equation constants. After zeroing the sample and subsequent testing of the unknown sample, this stray light is taken into account in the measurement.

The following experiment was run to demonstrate the ability of the art of this invention colorimeter to take stray light into account during a test measurement. It should be noted that an analyte which utilizes the blue region of the spectrum was chosen because this wavelength of light is more susceptible to erroneous answers because the intensity of the blue LED light is less intense than light coming from the higher wavelength regions. Therefore, any stay light could change results more dramatically.

The calorimeters were labeled Colorimeter 1, Colorimeter 2 and Colorimeter 3. A 1.00 ppm standard copper experiment was conducted with results averaged over 3 tests as follows:

| Colorimeter 1 Averaged Results: | Colorimeter 2 Averaged Results: | Colorimeter 3 Averaged Results: |
|---|---|---|
| Covered sample and receiving chamber (not exposed to ambient light) | | |
| 0.97 ppm | 0.99 ppm | 0.99 ppm |
| Uncovered sample and receiving chamber (exposed to ambient high intensity fluorescent light) | | |
| 0.97 ppm | 0.97 ppm | 0.99 ppm |

It can be seen from this example that stray light does not effect results using the colorimeter of this invention. The normalization process of this invention can factor in constant stray light conditions and thereby provide accurate results.

In all of the above examples it is important to note that only constants, the preferred radiation absorption equation and the normalization factor are stored in memory of colorimeter 2. No empirical data are stored. All samples tested under this curve fitting analysis derive results based on calculations and not on a look-up table of predetermined values. Hence, external parameters do not effect the test being conducted. Parameters such as temperature of colorimeter, detector life and alignment, LED life and alignment, battery voltage, temperature of reagents, etc. do not effect the results for the current technology. Further, these examples demonstrate LED producing radiation of different wavelengths that could be used to arrive at similar results. Many analytes, LED combinations, LED wavelengths and/or equations can be used to arrive at similar results using the process of this invention.

The foregoing constitutes a description of various features of a preferred embodiment. Many changes to the preferred embodiment are possible without departing from the spirit and scope of the invention. Therefore, the scope of this invention should be determined with reference not to the preferred embodiments but to the following claims.

We claim:

1. A process for quantitatively analyzing a gaseous or liquid medium by radiation absorption for a known analyte comprising the steps of:
   a. for said analyte establishing quantitative test data in the medium for said analyte using prepared standards;
   b. entering the test data into an electronic processor to establish multiple radiation absorption equations that conform to test data;
   c. selecting a preferred radiation absorption equation;
   d. entering said preferred radiation absorption equation into a data storage means which cooperates with a radiation absorption device.
   e. zero radiation device using single predetermined sample of said medium.
   f. measure the radiation absorption properties of said predetermined sample to develop a single constant that is used to normalize the radiation absorption equation; and
   g. position an unknown sample containing an analyte in said medium, in said radiation absorption device and evaluate the absorption properties of the unknown sample against the normalized radiation absorption equation.

2. The process of claim 1 wherein the radiation absorption data of the unknown sample is converted to electrical current and the voltage of said electrical current is measured on a calibrated voltmeter.

3. The process of claim 1 wherein the radiation absorption data of the unknown sample is converted to a digital waveform and the frequency of said digital waveform is measured.

4. The process of claim 3 wherein the radiation absorption equation used is a member selected from the group of linear equations, logistic model equations or exponential equations.

5. The process of claim 1 wherein the analyte is incorporated in a liquid medium and the analyte and liquid medium are treated with a reagent which alters the radiation absorption properties of the composite liquid medium analyte system.

6. The process of claim 5 wherein the liquid medium is water and the analyte is in solution.

7. The process of claim 6 wherein the radiation absorption equation used is a member selected from the group of linear equations, logistic model equations or exponential equations.

8. The process of claim 5 wherein the liquid medium is water and the analyte is a colloidal suspension.

9. The process of claim 8 wherein the radiation absorption equation used is a member selected from the group of linear equations, logistic model equations or exponential equations.

10. The process of claim 5 wherein the liquid medium is water and the analyte is a dissolved gas.

11. The process of claim 10 wherein the radiation absorption equation used is a member selected from the group of linear equations, logistic model equations or exponential equations.

12. The process of claim 5 wherein the radiation absorption equation is a member selected from the group of linear equations, logistic model equations or exponential equations.

13. The process of claim 1 wherein the medium is a gas and the analyte is a different gas which is mixed in the medium.

14. The process of claim 13 wherein the medium gas is air.

15. The process of claim 14 wherein the radiation absorption equation used is a member selected from the group of linear equations, logistic model equations or exponential equations.

16. The process of claim 13 wherein the radiation absorption equation used is a member selected from the group of linear equations, logistic model equations or exponential equations.

17. The process of claim 1 wherein the radiation absorption equation used is a member selected from the group of linear equations, logistic model equations or exponential equations.

* * * * *